(12) United States Patent
Miros et al.

(10) Patent No.: US 7,731,244 B2
(45) Date of Patent: Jun. 8, 2010

(54) MAKE-BRAKE CONNECTOR ASSEMBLY WITH OPPOSING LATCHES

(75) Inventors: Robert H J Miros, Fairfax, CA (US); Margaret Birmingham, Oakland, CA (US)

(73) Assignee: CoolSystems, Inc., Alameda, CA (US)

( * ) Notice: Subject to any disclaimer, the term of this patent is extended or adjusted under 35 U.S.C. 154(b) by 441 days.

(21) Appl. No.: 11/854,352

(22) Filed: Sep. 12, 2007

(65) Prior Publication Data
US 2009/0066079 A1    Mar. 12, 2009

(51) Int. Cl.
*F16L 37/00* (2006.01)

(52) U.S. Cl. .................. 285/317; 285/124.4; 285/124.3; 285/124.5

(58) Field of Classification Search .................. 285/308, 285/317, 124.4, 124.2, 124.3, 124.5
See application file for complete search history.

(56) References Cited

U.S. PATENT DOCUMENTS

| | | |
|---|---|---|
| 1,958,899 A | 5/1934 | MacAdams |
| 2,413,386 A | 12/1946 | Schulz |
| 2,510,125 A | 6/1950 | Meakin |
| 2,531,074 A | 11/1950 | Miller |
| 2,540,547 A | 2/1951 | Rodert |
| 2,608,690 A | 9/1952 | Kolb et al. |
| 2,703,770 A | 3/1955 | Melzer |
| 2,726,658 A | 12/1955 | Chessey |
| 3,261,042 A | 7/1966 | Baker |
| 3,320,682 A | 5/1967 | Sliman |
| 3,354,898 A | 11/1967 | Barnes |
| 3,561,435 A | 2/1971 | Nicholson |
| 3,738,367 A | 6/1973 | Hardy |
| 3,830,676 A | 8/1974 | Elkins |
| 3,871,381 A | 3/1975 | Roslonski |
| 3,901,225 A | 8/1975 | Sconce |
| 3,993,053 A | 11/1976 | Grossan |
| 4,026,299 A | 5/1977 | Sauder |
| 4,116,476 A | 9/1978 | Porter et al. |
| 4,118,946 A | 10/1978 | Tubin |
| 4,147,921 A | 4/1979 | Walter et al. |
| 4,149,529 A | 4/1979 | Copeland et al. |
| 4,149,541 A | 4/1979 | Gammons et al. |
| 4,194,247 A | 3/1980 | Melander |
| 4,338,944 A | 7/1982 | Arkans |
| 4,412,648 A | 11/1983 | Ford et al. |
| 4,436,125 A * | 3/1984 | Blenkush ..................... 141/330 |

(Continued)

FOREIGN PATENT DOCUMENTS

EP       1329676 A1       7/2003

(Continued)

OTHER PUBLICATIONS

Elkins, U.S. Appl. No. 09/173,637 entitled "Compliant heat exchange splint and control unit," filed Oct. 16, 1998.

(Continued)

*Primary Examiner*—David E Bochna
(74) *Attorney, Agent, or Firm*—Shay Glenn LLP (57) ABSTRACT

A make-break connector assembly having a latching mechanism integral to the top and bottom of the housing. The connector assembly includes connectors for fluid or air flow. The connector assembly has a single button release to release both the top and bottom latches.

13 Claims, 7 Drawing Sheets

U.S. PATENT DOCUMENTS

| | | | |
|---|---|---|---|
| 4,471,759 | A | 9/1984 | Anderson et al. |
| 4,478,436 | A | 10/1984 | Hashimoto |
| 4,547,906 | A | 10/1985 | Nishida et al. |
| 4,597,384 | A | 7/1986 | Whitney |
| 4,678,027 | A | 7/1987 | Shirey et al. |
| 4,691,762 | A | 9/1987 | Elkins et al. |
| 4,718,429 | A | 1/1988 | Smidt |
| 4,738,119 | A | 4/1988 | Zafred |
| 4,753,268 | A | 6/1988 | Palau |
| 4,765,338 | A | 8/1988 | Turner et al. |
| 4,884,304 | A | 12/1989 | Elkins |
| 4,925,603 | A | 5/1990 | Nambu |
| 4,955,435 | A | 9/1990 | Shuster et al. |
| 4,964,282 | A | 10/1990 | Wagner |
| 4,976,262 | A | 12/1990 | Palmacci |
| 5,002,270 | A | 3/1991 | Shine |
| 5,014,695 | A | 5/1991 | Benak et al. |
| 5,022,109 | A | 6/1991 | Pekar |
| 5,033,136 | A | 7/1991 | Elkins |
| 5,052,725 | A | 10/1991 | Meyer et al. |
| 5,072,875 | A | 12/1991 | Zacoi |
| 5,074,285 | A | 12/1991 | Wright |
| 5,076,068 | A | 12/1991 | Mikhail |
| 5,080,089 | A | 1/1992 | Mason et al. |
| 5,080,166 | A | 1/1992 | Haugeneder |
| 5,086,771 | A | 2/1992 | Molloy |
| 5,097,829 | A | 3/1992 | Quisenberry |
| 5,104,158 | A | 4/1992 | Meyer et al. |
| 5,113,877 | A | 5/1992 | Johnson, Jr. et al. |
| 5,163,425 | A | 11/1992 | Nambu et al. |
| 5,172,689 | A | 12/1992 | Wright |
| 5,201,552 | A | 4/1993 | Hohmann et al. |
| 5,230,335 | A | 7/1993 | Johnson, Jr. et al. |
| 5,241,951 | A | 9/1993 | Mason et al. |
| 5,243,706 | A | 9/1993 | Frim et al. |
| 5,269,369 | A | 12/1993 | Faghri |
| 5,294,156 | A | 3/1994 | Kumazaki et al. |
| 5,314,455 | A | 5/1994 | Johnson, Jr. et al. |
| 5,316,547 | A | 5/1994 | Gildersleeve |
| 5,353,605 | A | 10/1994 | Naaman |
| 5,354,101 | A | 10/1994 | Anderson, Jr. |
| 5,354,103 | A | 10/1994 | Torrence et al. |
| 5,383,689 | A | 1/1995 | Wolfe, Sr. |
| RE34,883 | E | 3/1995 | Grim |
| 5,395,399 | A | 3/1995 | Rosenwald |
| 5,407,421 | A | 4/1995 | Goldsmith |
| 5,411,541 | A | 5/1995 | Bell et al. |
| 5,415,625 | A | 5/1995 | Cassford et al. |
| 5,417,720 | A | 5/1995 | Mason |
| 5,427,577 | A | 6/1995 | Picchietti et al. |
| 5,441,533 | A | 8/1995 | Johnson et al. |
| 5,449,379 | A | 9/1995 | Hadtke |
| 5,451,201 | A | 9/1995 | Prengler |
| 5,466,250 | A | 11/1995 | Johnson, Jr. et al. |
| 5,470,353 | A | 11/1995 | Jensen |
| 5,494,074 | A * | 2/1996 | Ramacier et al. ........ 137/614.04 |
| 5,496,358 | A | 3/1996 | Rosenwald |
| 5,520,622 | A | 5/1996 | Bastyr et al. |
| 5,524,293 | A | 6/1996 | Kung |
| 5,527,268 | A | 6/1996 | Gildersleeve et al. |
| 5,533,354 | A | 7/1996 | Pirkle |
| 5,539,934 | A | 7/1996 | Ponder |
| 5,554,119 | A | 9/1996 | Harrison et al. |
| 5,556,138 | A | 9/1996 | Nakajima et al. |
| 5,564,124 | A | 10/1996 | Elsherif et al. |
| 5,630,328 | A | 5/1997 | Hise et al. |
| 5,645,671 | A | 7/1997 | Tillinghast |
| 5,683,118 | A | 11/1997 | Slocum |
| 5,792,216 | A | 8/1998 | Kappel |
| 5,833,638 | A | 11/1998 | Nelson |
| 5,865,841 | A | 2/1999 | Kolen et al. |
| 5,868,690 | A | 2/1999 | Eischen, Sr. |
| 5,913,885 | A | 6/1999 | Klatz et al. |
| 5,920,934 | A | 7/1999 | Hannagan et al. |
| 5,967,225 | A | 10/1999 | Jenkins |
| 5,968,072 | A | 10/1999 | Hite et al. |
| 5,970,519 | A | 10/1999 | Weber |
| 5,980,561 | A | 11/1999 | Kolen et al. |
| 5,984,885 | A | 11/1999 | Gaylord, Jr. et al. |
| 5,989,285 | A | 11/1999 | DeVilbiss et al. |
| 5,992,459 | A | 11/1999 | Sugita et al. |
| 6,030,412 | A | 2/2000 | Klatz et al. |
| 6,036,107 | A | 3/2000 | Aspen et al. |
| 6,053,169 | A | 4/2000 | Hunt |
| 6,083,256 | A | 7/2000 | Der Ovanesian |
| 6,105,382 | A | 8/2000 | Reason |
| 6,109,338 | A | 8/2000 | Butzer |
| 6,117,164 | A | 9/2000 | Gildersleeve et al. |
| 6,146,413 | A | 11/2000 | Harman |
| 6,156,059 | A | 12/2000 | Olofsson |
| 6,178,562 | B1 | 1/2001 | Elkins |
| 6,261,314 | B1 | 7/2001 | Rich |
| 6,306,112 | B2 | 10/2001 | Bird |
| 6,328,276 | B1 | 12/2001 | Falch et al. |
| 6,352,550 | B1 | 3/2002 | Gildersleeve et al. |
| 6,354,635 | B1 | 3/2002 | Dyson et al. |
| 6,361,514 | B1 | 3/2002 | Brown et al. |
| 6,368,357 | B1 | 4/2002 | Schon et al. |
| 6,371,976 | B1 | 4/2002 | Vrzalik et al. |
| 6,382,678 | B1 | 5/2002 | Field et al. |
| 6,443,498 | B1 | 9/2002 | Liao |
| 6,547,284 | B2 * | 4/2003 | Rose et al. ..................... 285/1 |
| 6,551,347 | B1 | 4/2003 | Elkins |
| 6,551,348 | B1 | 4/2003 | Blalock et al. |
| 6,645,232 | B2 | 11/2003 | Carson |
| 6,695,872 | B2 | 2/2004 | Elkins |
| 6,823,682 | B1 | 11/2004 | Jenkins et al. |
| 6,871,878 | B2 * | 3/2005 | Miros ...................... 285/124.5 |
| 6,926,311 | B2 * | 8/2005 | Chang et al. ................. 285/317 |
| 6,942,015 | B1 | 9/2005 | Jenkins |
| 7,008,445 | B2 | 3/2006 | Lennox |
| 7,107,629 | B2 | 9/2006 | Miros et al. |
| 7,198,093 | B1 | 4/2007 | Elkins |
| 7,306,568 | B2 | 12/2007 | Diana |
| 7,434,844 | B2 * | 10/2008 | Kao ........................... 285/317 |
| 7,448,653 | B2 * | 11/2008 | Jensen et al. ................. 285/307 |
| 7,490,620 | B2 * | 2/2009 | Tesluk et al. .............. 137/15.09 |
| 2001/0018604 | A1 | 8/2001 | Elkins |
| 2001/0034545 | A1 | 10/2001 | Elkins |
| 2001/0034546 | A1 | 10/2001 | Elkins |
| 2001/0039439 | A1 | 11/2001 | Elkins et al. |
| 2002/0019657 | A1 | 2/2002 | Elkins |
| 2004/0167594 | A1 | 8/2004 | Elkins |
| 2005/0143796 | A1 | 6/2005 | Augustine et al. |
| 2005/0143797 | A1 | 6/2005 | Parish et al. |
| 2005/0256556 | A1 | 11/2005 | Schirrmacher et al. |
| 2006/0200057 | A1 | 9/2006 | Sterling |
| 2007/0161932 | A1 | 7/2007 | Pick et al. |
| 2007/0282230 | A1 | 12/2007 | Valderrabano et al. |
| 2008/0058911 | A1 | 3/2008 | Parish et al. |
| 2008/0195012 | A1 | 8/2008 | Miros et al. |
| 2009/0005841 | A1 | 1/2009 | Schirrmacher et al. |

FOREIGN PATENT DOCUMENTS

| | | | |
|---|---|---|---|
| IT | | 330552 | 10/1935 |
| WO | | WO92/13506 A1 | 8/1992 |
| WO | | WO92/15263 A1 | 9/1992 |
| WO | | WO94/09732 A1 | 5/1994 |
| WO | | WO96/26693 A1 | 9/1996 |
| WO | | WO98/07397 A1 | 2/1998 |
| WO | | WO99/44552 A1 | 9/1999 |
| WO | | WO00/23016 A1 | 4/2000 |
| WO | | WO00/55542 A1 | 9/2000 |

| | | |
|---|---|---|
| WO | WO00/67685 A1 | 11/2000 |

OTHER PUBLICATIONS

Lowe et al.; U.S. Appl. No. 12/329,461 entitled "Cooling system having bypass valve to regulate fluid flow," filed Dec. 5, 2009.

Tomlinson et al., U.S. Appl. No. 12/329,481 entitled "Therapeutic cooling and/or heating system including a thermo-conductive material," filed Dec. 5, 2009.

BioCompression Systems, Inc. (Moonachie, NJ); Product literature for Sequential Circulators; 15 pgs.

\* cited by examiner

FIG. 6(B) SECTION D-D

FIG. 5(A)

FIG. 5(B) SECTION C-C

MAKE-BRAKE CONNECTOR ASSEMBLY WITH OPPOSING LATCHES

BACKGROUND OF THE INVENTION

1. Field of the Invention

The present invention relates generally to connector assemblies, such as connector assemblies for liquid and/or air flow.

2. Description of the Related Art

It is now common to apply cold and compression to a traumatized area of a human body to facilitate healing and prevent unwanted consequences of the trauma. Cold packing with ice bags or the like traditionally has been used to provide deep core cooling of a body part. Elastic wraps are often applied to provide compression. It will be appreciated that these traditional techniques are quite uncontrollable. For example, the temperature of an ice pack will, of course, change when the ice melts, and it has been shown that the application of elastic wraps and, consequently, the pressure provided by the same, varies considerably even where the wrappers are experienced individuals. Because of these and other difficulties, many in the field have turned to more complex arrangements which include cooling units for maintaining a desired temperature through a splint or other heat exchanger. Some of these units also provide compressive pressure.

Prior art connectors that attach heat exchangers to a controller that supplies air flow and liquid flow are problematic. They are problematic because: (a) the connectors are not easily operated (i.e., the connections are not easily made or broken); (b) users cannot readily appreciate how to orient the connector for making the connection; and (c) a mistake in a user identifying a type of heat exchanger can cause it be connected to a controller that may, for example, supply too high a pressure for liquid and/or air flow and, thereby, raise safety issues.

A prior connector apparatus is disclosed in U.S. Pat. No. 6,871,878. As described therein, at least one of the connectors in the housing includes a latching structure to securely latch the connector apparatus to a mating component. However, connectors having an integrated latching structure are relatively more expensive to manufacture, and require more precise alignment of respective mating components.

SUMMARY OF THE INVENTION

In one embodiment, the present invention is a connector assembly comprising:
 a top housing shell having a top latch opening and latch release button opening;
 a bottom housing shell having a bottom latch opening;
 a top latch assembly affixed to the top housing shell, the top latch assembly comprising:
  a latch release button;
  a top latch; and
  at least one elongated arm;
  wherein the top latch extends through the top latch opening in the top housing shell, and the latch release button extends through the latch release button opening;
 a bottom latch assembly affixed to the bottom housing shell; wherein the bottom latch assembly comprises a bottom latch; and wherein the at least one elongated arm of the top latch assembly contacts the bottom latch assembly;
 a top spring located between the top latch assembly and the top housing shell;
 a bottom spring located between the bottom latch assembly and the bottom housing shell;
 a front wall;
 at least one connector attached to the front wall for connecting at least one fluid or air flow channel; and
 a tube opening in a rear area of the top and bottom housing shells.

In another embodiment, the present invention is connector assembly comprising:
 a top housing shell having a top latch opening and latch release button opening;
 a bottom housing shell having a bottom latch opening;
 a top latch assembly affixed to the top housing shell, the top latch assembly formed as a unitary piece and comprising:
  a latch release button;
  a top latch;
  two alignment and pivot extensions on each side of the top latch; and
  two elongated arms on a bottom portion of the latch assembly;
  wherein the top latch extends through the top latch opening in the top housing shell, and the latch release button extends through the latch release button opening;
 a bottom latch assembly formed as a unitary piece affixed to the bottom housing shell; wherein the bottom latch assembly comprises:
  a bottom latch; and
  two alignment and pivot extensions on each side of the bottom latch;
  wherein the two elongated arms of the top latch assembly contact the bottom latch assembly at a raised portion thereof;
 a top spring located between the top latch assembly and the top housing shell;
 a bottom spring located between the bottom latch assembly and the bottom housing shell;
 a front wall;
 three poppet-valve style connectors attached to the front wall for connecting two fluid and air flow channel, wherein one of the connectors is offset relative to the other two connectors on the front wall; and
 a tube opening in a rear area of the top and bottom housing shells; wherein the top shell housing comprises two pivot receptacles to hold the pivot and alignment extensions on the top latch assembly; and the bottom shell housing comprises two pivot receptacles to hold the pivot and alignment extensions on the bottom latch assembly.

With such a configuration, the present invention includes a single-sided latch release. In addition, since the latch mechanism is integral to the housing, the actual connectors do not require a separate latching mechanism.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF THE INVENTION

The following description is provided to enable any person skilled in the art to make and use the invention and sets forth the best modes contemplated by the inventor for carrying out the invention. Various modifications, however, will remain readily apparent to those skilled in the art. Any and all such modifications, equivalents and alternatives are intended to fall within the spirit and scope of the present invention.

Figure 1:
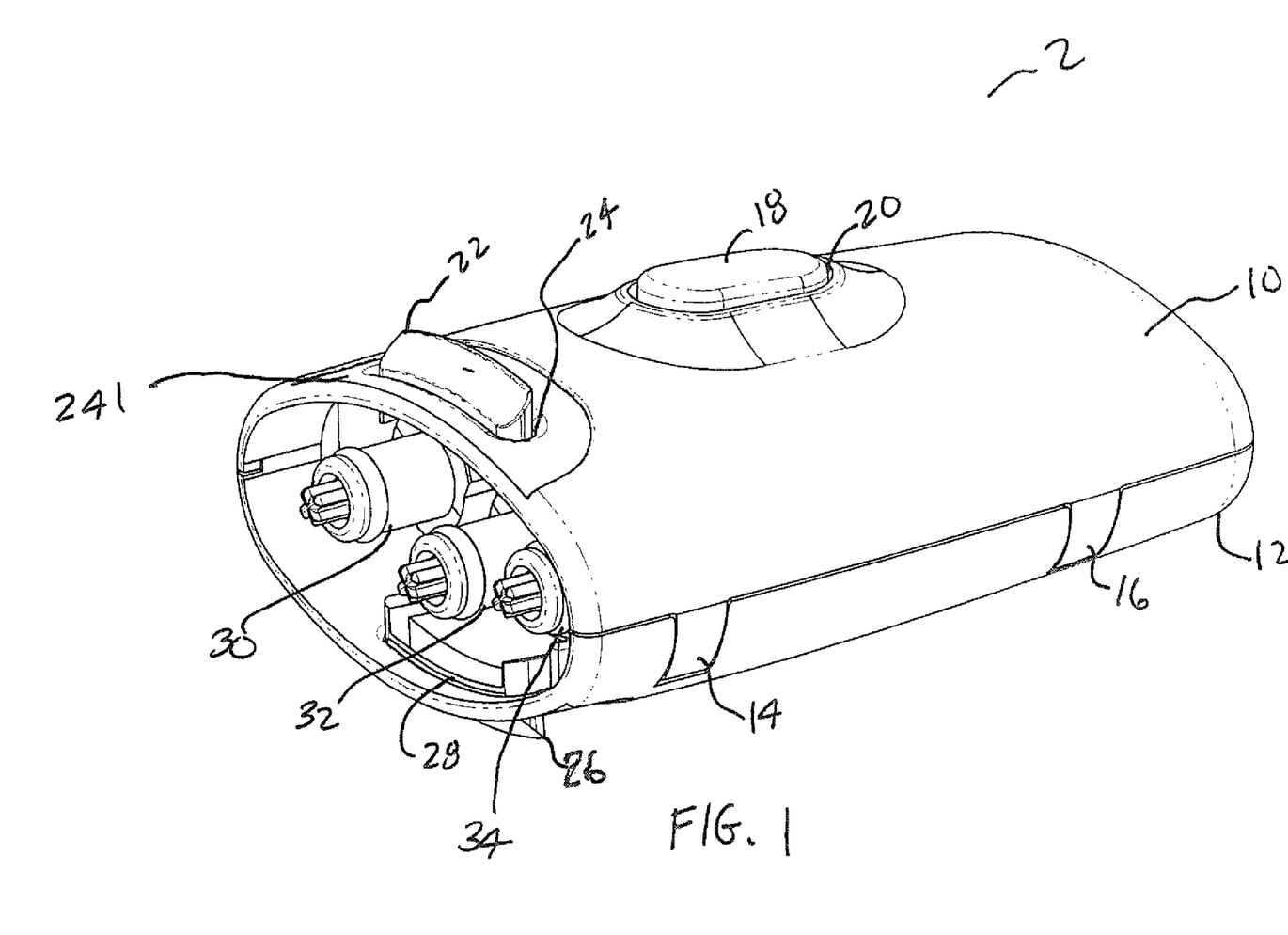
FIG. 1 is a perspective view of a connector assembly according to one embodiment of the present invention.

FIG. 1 is a perspective view of a make-break connector assembly 2 according to one embodiment of the present invention. The present invention will be described with respect to this preferred embodiment, but the description of this particular embodiment is not intended to limit the scope of the present invention. The connector assembly 2 is adapted to interface to a heat exchanger, for example, and without limitation, a heat exchanger: (a) to which is flowed, for example, and without limitation, air and/or liquid (which air and/or liquid may be flowed, for example, under pressure), and (b) from which is flowed the liquid after circulation in the heat exchanger.

One example of a heat exchanger that might utilize this embodiment of the present invention is a human body heat exchanger of a type comprising two overlapping bladders. In such a type of human body heat exchanger, a first bladder (for flow and distribution of a heat exchange liquid) is overlapped by a second bladder (for flow of air or some other gas to provide pressure for compression, and to assure good and intimate contact of the first bladder with a body part). Although air or some other gas could also be used in place of the heat exchange liquid, in most situations it is desirable to use a liquid because, among other reasons, of its thermal capacity. In such a construction, two connectors are utilized for the flow of the heat exchange liquid (a delivery path and a return path), and one connector provides air pressure for compression.

As shown in FIG. 1, the connector assembly 2 comprises a top shell housing 10 and bottom shell housing 12. The top shell housing 10 and bottom shell 12 housing are fabricated, for example, and without limitation, by molding high impact plastic such as polycarbonate plastic in accordance with any one of a number of methods that are well known to those of ordinary skill in the art (other suitable materials include various plastics and metals and combinations thereof). In accordance with one embodiment of the present invention, when the top shell housing 10 and the bottom shell housing 12 are assembled to the connector assembly 2, a front surface of the top shell housing 10, and a front surface of the bottom shell housing 12 lie substantially in a plane.

The top shell housing 10 includes side tabs 14, 16 which interlock with the bottom shell housing 12. The top shell housing 10 further includes an opening 20 for a latch release button 18, and a latch opening 24 for a top latch 22. Similarly, the bottom shell housing 12 includes a latch opening 28 for a bottom latch 26. The front of the connector assembly 2 includes three connectors 30, 32, 24. Generally, the two outside connectors 30, 34 are aligned within the mouth of the assembly, whereas the middle connector 32 is offset below a center line of the two outside connectors 30, 34. In a preferred embodiment, an area 241 around the top latch opening 24 is indented. This area 241 acts a "key" for mating with a complementary mating component.

Figure 2:
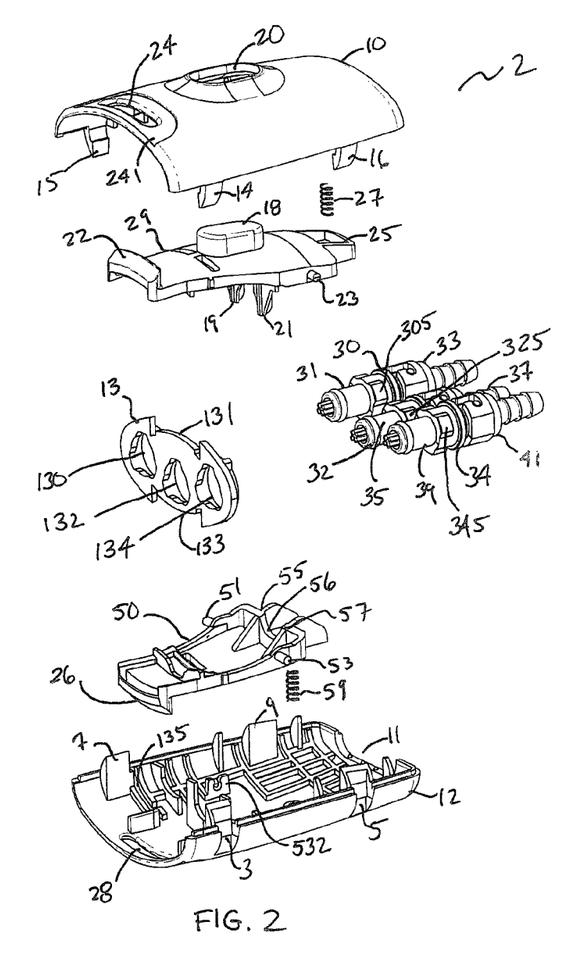
FIG. 2 is an exploded view of the connector assembly of FIG. 1.

FIG. 2 is an exploded view of the connector assembly 2 illustrated in FIG. 1. As previously described, the top shell housing 10 includes a latch release button opening 20, a latch opening 24, and side tabs 14, 16. The top shell housing 10 also includes two additional side tabs on the back side of the housing (only a front tab 15 is shown). The bottom shell housing 12 includes a latch opening 28, and a rear opening 11 (a corresponding rear opening (not shown) is located on the rear of the top shell housing 10). The bottom shell housing also has side indentations 3, 5, 7, 9 for interlocking the top shell housing 10 to the bottom shell housing with the side tabs 14, 16, 15, 17, respectively.

Figure 4A:
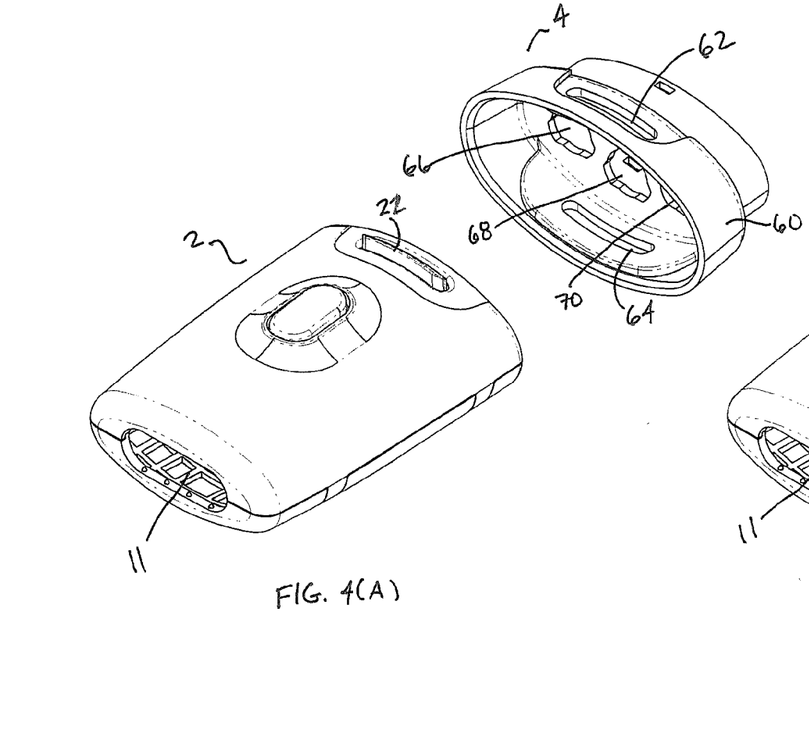
FIGS. 4(A) and 4(B) illustrate a perspective view of the connector assembly with different embodiments of a corresponding mating assembly.
Figure 4B:
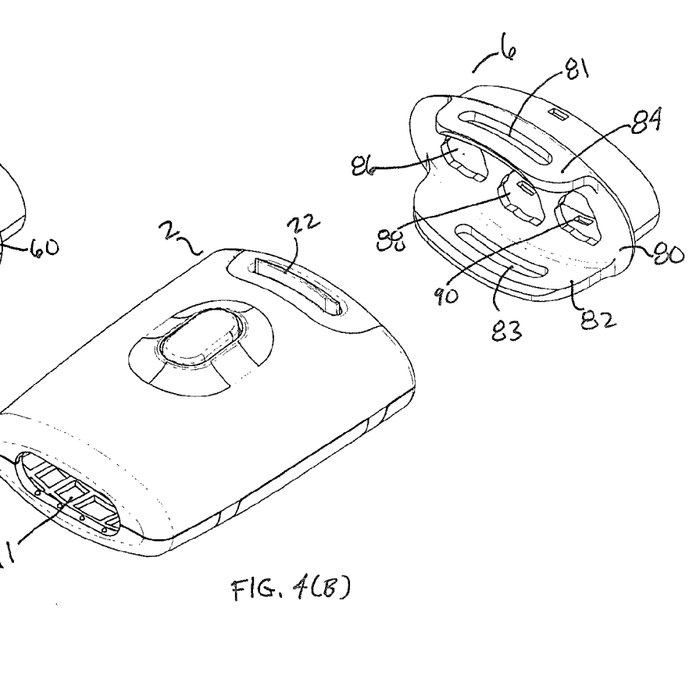

A top latch assembly 29 is formed as a single molded component. The top latch assembly 29 is formed with a latch release button 18, which protrudes through the latch release button opening 20 when assembled. The top latch assembly 29 further includes a latch 26 formed generally with a straight back, and a beveled front edge to lockingly engage a corresponding mating opening (as shown in FIGS. 4(A) and 4(B)). The latch 26 extends through the latch opening 24 on the top shell housing 10 when assembled. The top latch assembly further includes a rear portion 25, a side alignment and pivot extension 23 (and one not shown). These alignment and pivot extensions fit into corresponding receptacles on the top shell housing 10. On the bottom of the top latch assembly 29, two elongated arms 19, 21 extend down to contact the bottom latch assembly 50 (described below). The elongated arms 19, 21 are spaced to allow a connector 32 to fit in between the arms 19, 21. A spring 27 provides a tension force between the rear portion of the top latch assembly 29 and the top shell housing 10.

A bottom latch assembly 50 is formed with a latch 26 having a generally straight back, and beveled front edge to lockingly engage a corresponding mating opening (as shown in FIGS. 4(A) and 4(B)). The bottom latch assembly has rear projections 55, 57. An area 56 between the projections 55, 57 provides an opening for the center connector 32. Side alignment and pivot projections 51, 53 fit into corresponding receptacles on the bottom shell housing 12. A spring 59 provides a tension force between the bottom latch assembly 50 and the bottom shell housing 12.

A front wall 13 is formed as a separate piece, and has three openings 130, 132, 134 for the three connectors 30, 32, 34, respectively. Each opening has a "keyed" notch to allow a connector to be inserted, and then twisted to be held in place. As mentioned previously, the center connector opening 132 is offset below a center line of the two outer openings 130, 134. By offsetting the center connector 32, it insures that the connector assembly 2 can only be connected to a corresponding mating assembly in the correct orientation.

The front wall 13 includes a top notch 131 and a bottom notch 133. In operation, these notches 131, 133 provide space for the movement of the top latch assembly 29, and the bottom latch assembly 50. The front wall 13 is secured in a slot 135 on the bottom shell housing 12, and a similar slot (136, FIG. 8) on the top shell housing 10.

Figure 5A:
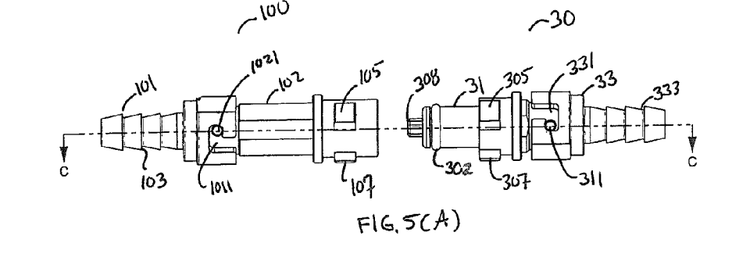
FIG. 5(A) illustrates a connector from the connector assembly and a connector from a corresponding mating assembly, according to one embodiment of the present invention.
Figure 5B:
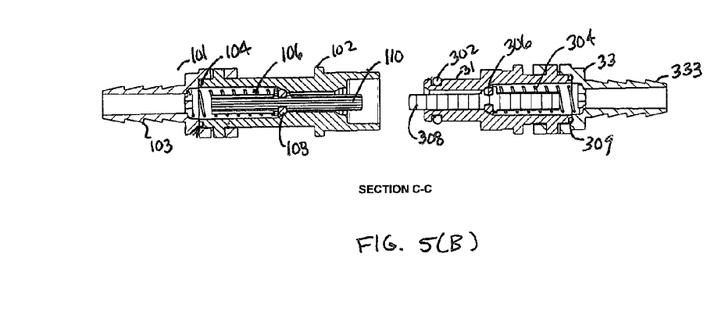
FIG. 5(B) is a cross-sectional view of the mating connectors of FIG. 5(A)
Figure 6A:
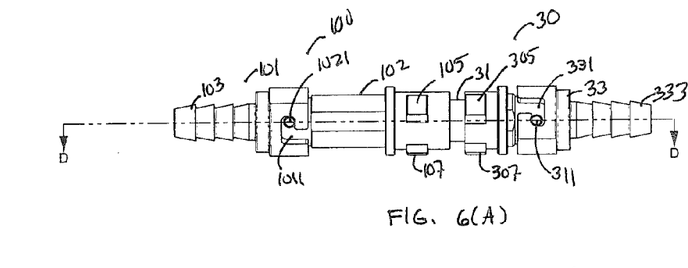
FIG. 6(A) is a perspective view of the connectors of FIG. 5(A) when connected.
Figure 6B:
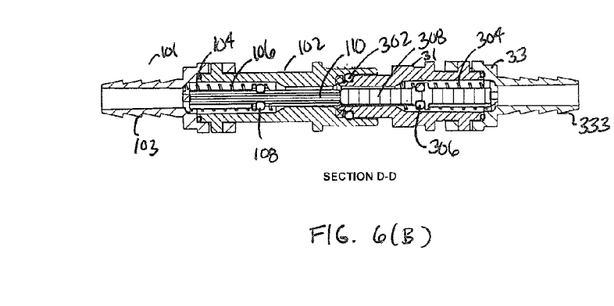
FIG. 6(B) is a cross-sectional view of the connectors of FIG. 6(A)

The preferred embodiment of the connector assembly 2 includes three connectors 30, 32, 34. The connectors 30, 32, 34 are held in place in the front wall 13 by keyed protrusions (for example protrusions 305, 325, 345). Each connector may have more than one such protrusion to interface with notches in the openings in the front wall 13. Once each connector 30, 32, 34 is aligned and inserted into the front wall 13, the connector is twisted to lock the connector in place. Further details of the connectors 30, 32, 34 are shown in FIGS. 5-7 and described below.

In operation, when the latch release button 18 is depressed, the top latch 22 is lowered into the latch opening 22, thereby releasing the top latch. The elongated arms 19, 21 of the top latch assembly 29 press against the bottom latch assembly 50, just in front of the rear projections 55, 57. This causes the bottom latch assembly to pivot, thereby causing the lower latch 26 to move into the lower latch opening 28. Thus, both the top latch 22 and the bottom latch 26 are released by pressing a single latch release button 18.

Figure 3A:
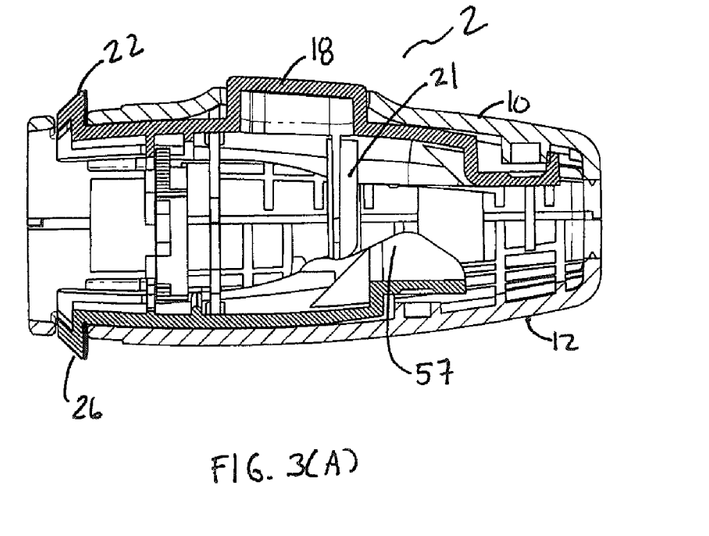
FIGS. 3(A) and 3(B) are side cross-sectional views of the connector assembly of FIG. 1, illustrating the operation of the latching mechanism.
Figure 3B:
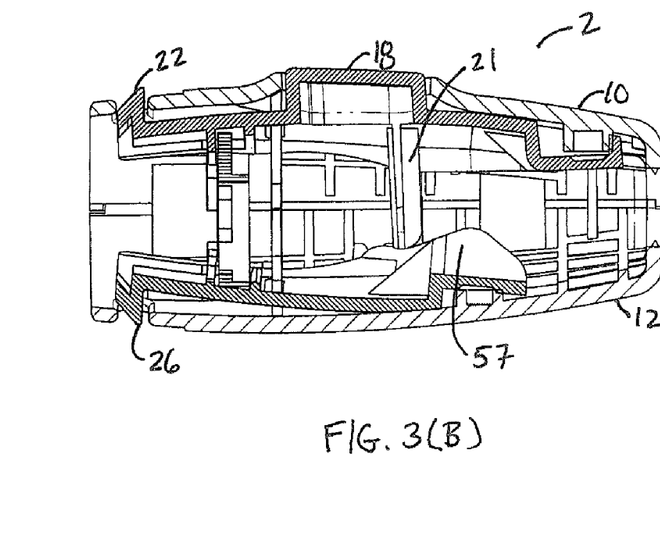

FIG. 3(A) is a cross-sectional view of the connector assembly illustrating the normal position of the latches 22, 26 when the latch release button 18 is not being pressed. As can be seen in cross-section, an elongated arm 21 on the upper latch assembly contacts the lower latch assembly at a point just in front of the rear projection 57. When the latch release button 18 is depressed, as shown in FIG. 3(B), the top latch 22 is forced down. The elongated arm 21 presses against the lower latch assembly, thereby causing it to pivot, which in turn raises the lower latch 26.

FIG. 4(A) is a perspective view of one embodiment of a mating interface 4 for the connector assembly 2. Specifically, a mating interface 4 has a shroud 60 with a top latch receptacle 62 and a bottom latch receptacle 64. The mating interface 4 further includes connector openings for holding mating connectors (not shown) for the connectors 30, 32, 34 in the connector assembly 2. When the connector assembly 2 is positioned into the mating interface 4, the top latch 22 mates with the top latch opening 62, and the bottom latch 26 mates with the bottom latch opening 64. When the latch release button is depressed, the top and bottom latches 22, 26 are released form their respective openings 62, 64.

FIG. 4(B) is a perspective view of an alternate embodiment of a mating interface 6. Instead of having a shroud 60, which surrounds the connector assembly 2, this embodiment includes a face 80 having top and bottom tabs 84, 82. The tabs include latch openings 81, 83 for receiving the top and bottom latches 22, 26. But unlike the embodiment of FIG. 4(A), the sides of the interface are open.

FIG. 5(A) illustrates the arrangement of a representative connector 30 in the connector assembly 2 and a representative connector 100 in a compatible mating interface 4, 6, such as those illustrated in FIGS. 4(A) and 4(B). Note that in the embodiments disclosed in the figures, three connectors are used, but the present invention may be implemented with more or fewer connectors in the connector assembly 2.

Connector 30 comprises two components. A rear hose barb portion 33 includes, for example, 1/8" hose barbs 333, and a front "bayonet" style coupling 331. The front component 31 includes a front spring-loaded valve 308 (i.e. a "poppet valve"), a post 311 for interlocking with the rear hose barb portion 33, and raised portions 305, 307 for interlocking the connector 30 with the front wall 13. The front component also includes an external O-ring 302 to provide a tight seal when coupled with connector 100.

Connector 100 includes a similar rear hose barb portion 101, including, for example, 1/8" hose barbs 101, and a front bayonet style coupling 1011. The front portion 102 includes raised portions 105, 107 for interlocking the connector 100 to a mating interface 4, 6.

These connectors 30, 100 are shown in further detail in the cross-section views of FIG. 5(B). Specifically, the connector assembly 2 connector 30 includes an internal spring 304, and an internal O-ring 306. When the connector 30 is not connected, the spring 302 forces valve 308 forward against an internal stop, effectively sealing off the internal flow channel through connector 30. Another O-ring 309 seals the front 31 and rear 33 portions of the connector 30.

Connector 100 also includes an internal spring 106, which forces valve 110 forward against an internal stop and an O-ring 108, to seal off the internal flow channel. Another O-ring 104 seals the front 102 and rear 101 portions of connector 100. Thus, as shown, when the two connectors 30, 100 are not connected any fluid or air flow is blocked on both sides.

FIGS. 6(A) and 6(B) show the connectors 30, 100 of FIG. 5 when they are attached. As shown in FIG. 6(B), when the connectors 30, 100 are attached, each valve 110, 308 is forced back, away from the internal stop, thereby allowing fluid and/or air to pass through the internal channel. Upon separation, however, the internal springs 108, 304, force the valves 110, 308 quickly back into a sealing position, thereby preventing leaking.

Figure 7:
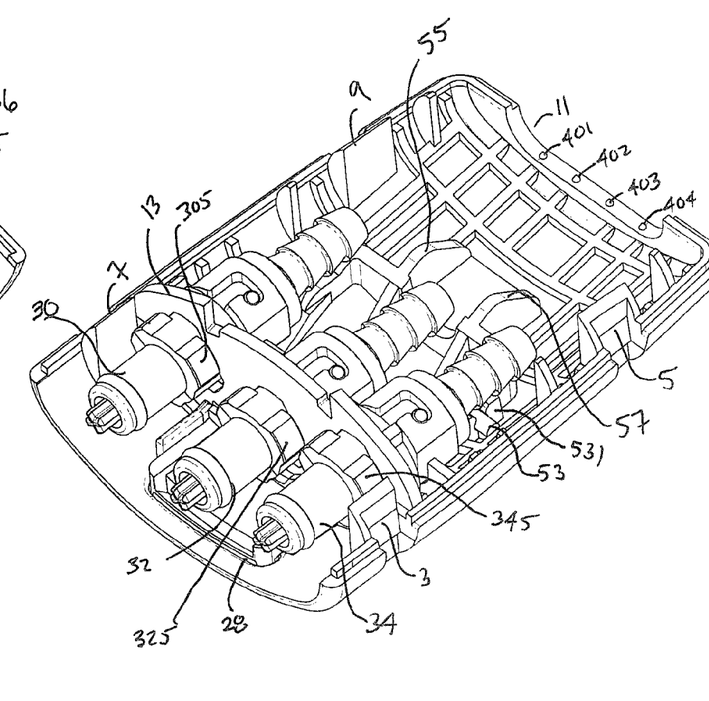
FIG. 7(A) is a perspective view of the connector components from the connector assembly.
FIG. 7(B) is a perspective view of the connector components from the mating assembly.
Figures 7A, 7B:
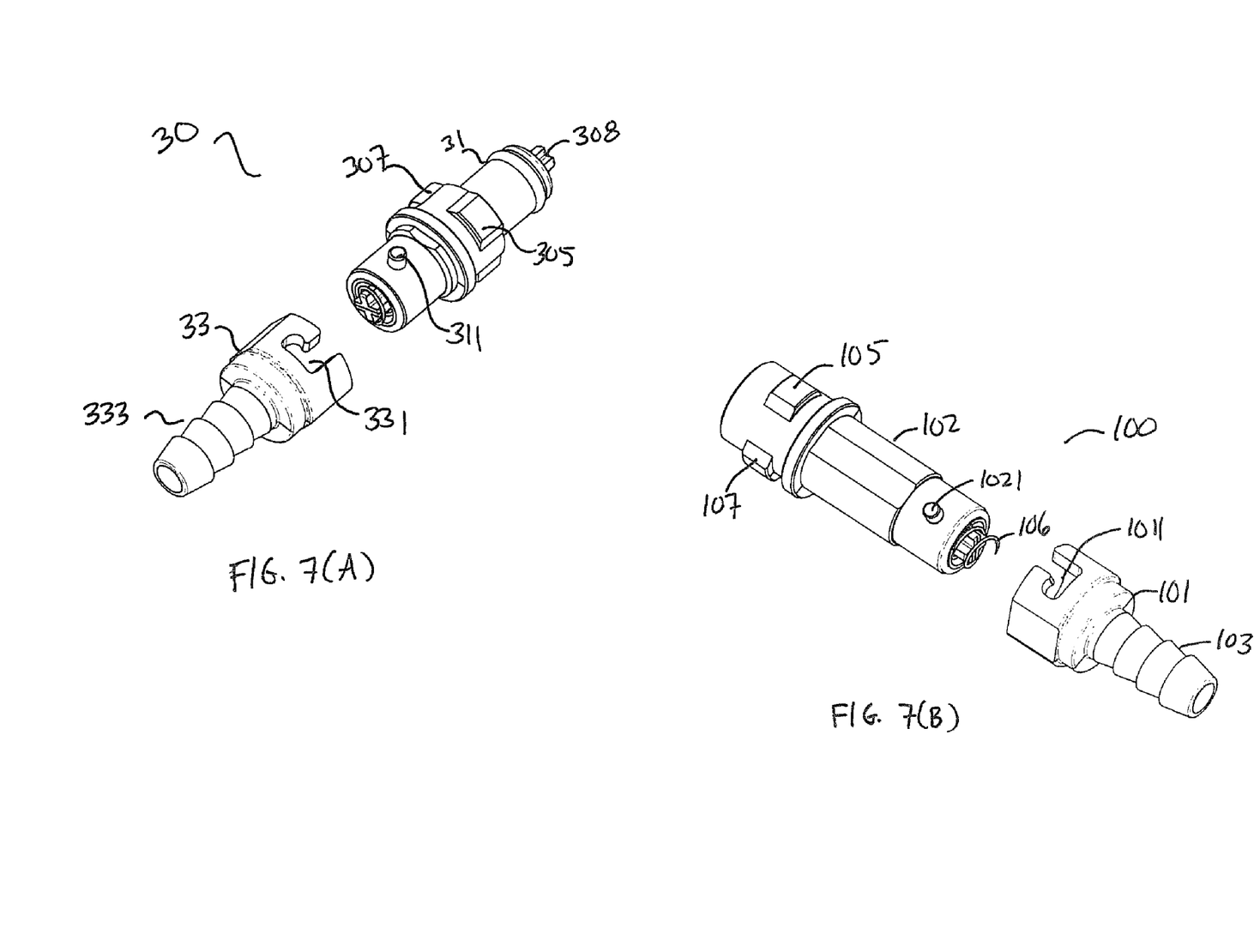

FIG. 7(A) shows the connector 30 in perspective view, with the two portions 31, 33 disconnected. Similarly, FIG. 7(B) is a perspective view of connector 100, showing its two components 102, 101 disconnected.

Figure 8:
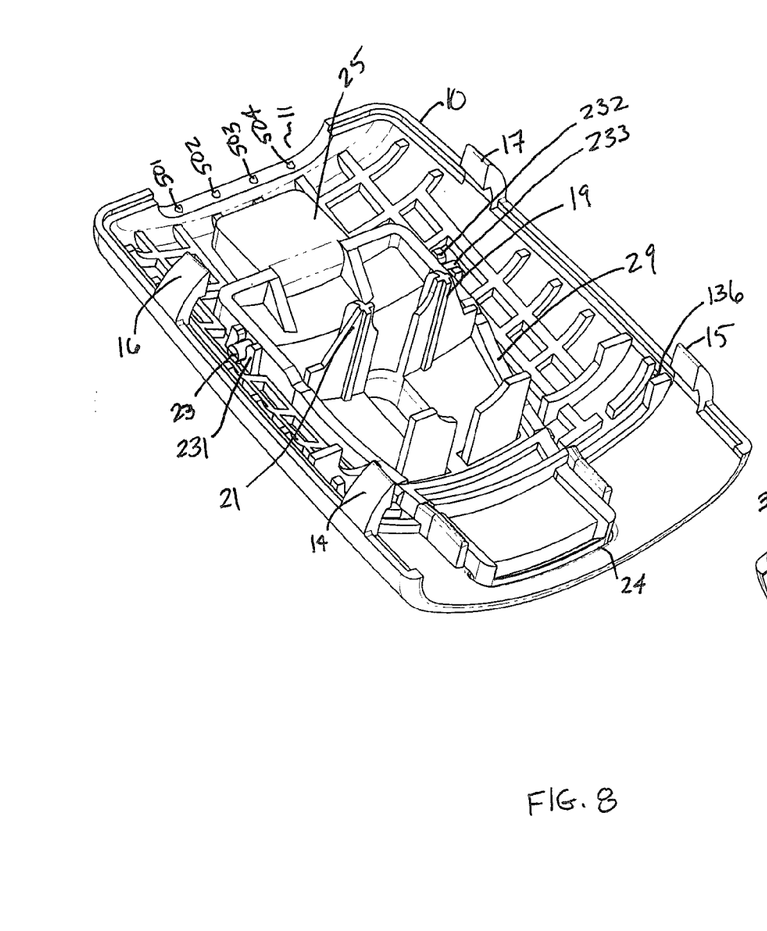
FIG. 8 is a top view of the inside of the top and bottom pieces of the connector assembly housing.

FIG. 8 shows an internal top perspective view of the connector assembly 2, with the top shell housing 10 and the bottom shell housing 12 separated. The front wall 13 is mounted into a slot on the bottom shell housing 12, and holds the three connectors 30, 32, 34. In assembly, a corresponding slot 136 on the top shell housing 10 locks the front wall 13 in place. The top latch assembly 29 is attached to the top shell housing 10 by pivot receptacles 231, 232 which hold the alignment and pivot protrusions 23, 233. Similarly, the bottom latch assembly 50 is held in place in the bottom shell housing 12 by similar pivot receptacles (for example receptacle 531 holding pivot protrusion 53).

At the rear of each housing is an opening 11. This opening 11 allows tubes to attach to the connectors 30, 32, 34, and secures the tubes, or tube sheathing, in place via raised bumps 401, 402, 403, 501, 502, 503, on each housing. As illustrated, the top shell housing 10 and the bottom shell housing 12 are snapped together and held by the side tabs 14, 15, 16, 17 interlocking with the corresponding recesses 3, 5, 7, 9. However, the top and bottom shell housing may be attached with screws in addition to the tabs, or instead of the tabs.

As described herein, when the connector assembly 2 is attached to a mating interface 4, 6, the latches 22, 26 lock the connector assembly 2 in place, and cause the valves in the connectors 30, 32, 36 to be forced open against their corresponding mating valves. When the latch release button 18 is depressed, the latches 22, 26 release from the mating interface 4, 6, and the valves are forced closed by the internal springs, thereby sealing each side. Thus, the present invention provides a make-break connection, without requiring latching structures on the actual connectors themselves.

One advantage of the present invention includes a single-sided latch release. In addition, since the latch mechanism is integral to the housing, the actual connectors do not require a separate latching mechanism.

Also, if desired, the latches 22, 26 and corresponding latch openings on a mating interface can be constructed such that the latches will "break away" from the mating interface if the connector and/or tubing is pulled with sufficient force. This can provide protection against damaging the equipment or tubing, in the case of an accidental separation of the connector assembly and mating interface. In practice, it is envisioned that the connector assembly 2 will be connected to each end of a length of tubing. One side connects to a heat-exchange wrap, and the other side to a control unit. In such a configuration, the system can be designed such that the connector assembly that connects to the control unit will hold with greater force than the connector assembly that holds to the wrap. In other words, the connector assembly on the wrap will pull loose first to avoid damaging the control unit.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A connector assembly comprising:
   a top housing shell having a top latch opening and latch release button opening;
   a bottom housing shell having a bottom latch opening;
   a top latch assembly affixed to the top housing shell, the top latch assembly comprising:
     a latch release button;
     a top latch; and
     at least one elongated arm;
     wherein the top latch extends through the top latch opening in the top housing shell, and the latch release button extends through the latch release button opening;
   a bottom latch assembly affixed to the bottom housing shell; wherein the bottom latch assembly comprises a bottom latch;
   a top spring located between the top latch assembly and the top housing shell;
   a bottom spring located between the bottom latch assembly and the bottom housing shell;
   a front wall;
   at least one connector attached to the front wall for connecting at least one fluid or air flow channel; and
   a tube opening in a rear area of the top and bottom housing shells;
   wherein the at least one elongated arm of the top latch assembly contacts the bottom latch assembly such that the bottom latch is controlled by the latch release button on the top latch assembly.

2. The connector assembly of claim 1, wherein the top latch assembly is a unitary piece.

3. The connector assembly of claim 2, wherein the top latch assembly comprises:
   a main body having a front section, a middle section, and a rear section; and
   two alignment and pivot extensions on each side of the main body;
   wherein the latch is formed on the front section of the main body, the latch comprising a generally straight back, and a beveled front edge;
   wherein the latch release button is formed on a top of the middle section of the main body; and
   wherein the at least one elongated arm comprises two elongated arms formed on a bottom of the middle section of main body.

4. The connector assembly of claim 3, wherein the top housing shell comprises two pivot receptacles to hold the pivot and alignment extensions on the top latch assembly.

5. The connector assembly of claim 1, wherein the bottom latch assembly is a unitary piece.

6. The connector assembly of claim 5, wherein the bottom latch assembly comprises:
   a main body;
   two alignment and pivot extensions on each side of the main body;
   wherein the latch is formed on the front section of the main body, the latch comprising a generally straight back, and a beveled front edge;

7. The connector assembly of claim 6, wherein the bottom shell housing comprises two pivot receptacles to hold the pivot and alignment extensions on the bottom latch assembly.

8. The connector assembly of claim 1, wherein the at least one connector comprises three poppet-valve style connectors, two of the connectors for fluid and one connector for air.

9. The connector assembly of claim 8, wherein one of the connectors is offset relative to the other two connectors on the front wall.

10. The connector assembly of claim 8, wherein each connector comprises a front poppet-valve style connector, and a rear portion having a hose barb section.

11. The connector assembly of claim 1, wherein the top housing shell further comprises four tabs, and the bottom housing shell comprises four side indentations corresponding to the four tabs, such that the top housing shell interlocks with the bottom housing shell.

12. The connector assembly of claim 1, wherein the opening in the rear area of the top and bottom shell housing comprises a plurality of raised bumps to hold tubing in place.

13. A connector assembly comprising:
   a top housing shell having a top latch opening and latch release button opening;
   a bottom housing shell having a bottom latch opening;
   a top latch assembly affixed to the top housing shell, the top latch assembly formed as a unitary piece and comprising:
     a latch release button;
     a top latch;
     two alignment and pivot extensions on each side of the top latch; and
     two elongated arms on a bottom portion of the latch assembly;
     wherein the top latch extends through the top latch opening in the top housing shell, and the latch release button extends through the latch release button opening;
   a bottom latch assembly formed as a unitary piece affixed to the bottom housing shell; wherein the bottom latch assembly comprises:
     a bottom latch; and
     two alignment and pivot extensions on each side of the bottom latch;
     wherein the two elongated arms of the top latch assembly contact the bottom latch assembly at a raised portion thereof such that the bottom latch is controlled by the latch release button on the top latch assembly;
   a top spring located between the top latch assembly and the top housing shell;
   a bottom spring located between the bottom latch assembly and the bottom housing shell;

a front wall;

three poppet-valve style connectors attached to the front wall for connecting two fluid and one air flow channel, wherein one of the connectors is offset relative to the other two connectors on the front wall; and a tube opening in a rear area of the top and bottom housing shells;

wherein the top shell housing comprises two pivot receptacles to hold the pivot and alignment extensions on the top latch assembly; and the bottom shell housing comprises two pivot receptacles to hold the pivot and alignment extensions on the bottom latch assembly.

* * * * *